May 6, 1975 H. L. BOLL Plant Pat. 3,714

STRAWBERRY PLANT

Filed Nov. 14, 1973

United States Patent

Plant Pat. 3,714
Patented May 6, 1975

3,714
STRAWBERRY PLANT

Herschel L. Boll, R.R. 4, Champaign, Ill. 61820

Filed Nov. 14, 1973, Ser. No. 415,497
Int. Cl. A01h *5/03*
U.S. Cl. Plt.—48 1 Claim

My invention relates to a new and distinct variety of strawberry plant. It is the result of a cross of [(Canall × Twentieth Century) × Twentieth Century] × Ogallala, made by me in 1967, at Champaign, Ill.

Since my discovery of the original plant, I have asexually reproduced a large number of plants from the original mother plant by rooted runners.

My object in the asexual propagation of the original mother plant was to determine the characteristics of the plant and of its fruit by the testing of a large number of plants. The distinguishing features of my new variety have proved to be permanent. My new variety has proved itself to have unusual possibilities because of its high productivity, its vigorous growth, and its early season of maturity.

Figure 1:
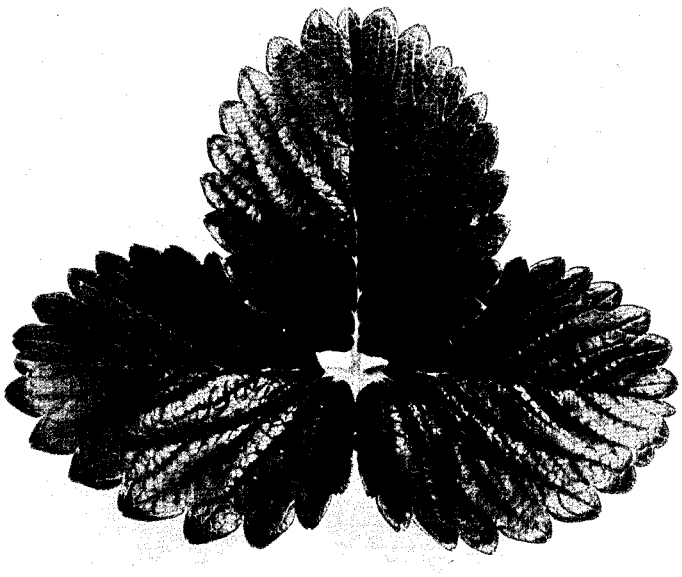
FIG. 1 shows a typical leaf in full color.
Figure 2:
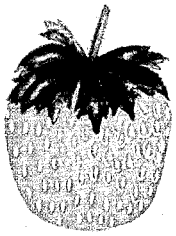
FIG. 2 is a berry of typical wedge shape.
Figure 3:
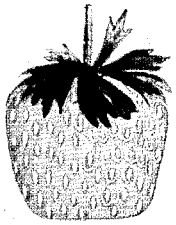
FIG. 3 shows a berry of typical blunt-wedge shape.
Figure 4:
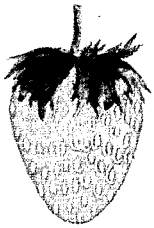
FIG. 4 illustrates a berry of typical conic shape.
Figure 5:
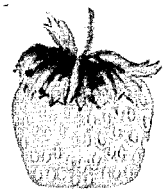
FIG. 5 shows a berry of typical blunt-conic shape.

In general, the distinct and new variety of strawberry plant, which is the subject of my invention and discovery, is characterized by its high productivity, by its vigorous growth, and by its early season of maturity. These characteristics I now refer to in greater detail. Color plate references are according to Color Standards and Color Nomenclature by Robert Ridgway.

Under the conditions at Champaign, Ill., my new variety of plant is June-bearing and high in productivity. A two-year-old plant has produced as many as 35 ripe berries at one picking, on 18 fruit stems. A one-year-old plant has produced as many as 15 ripe berries at one picking, on 8 fruit stems. The plants are vigorous, and are medium in height. They produce a medium number of runners, making a moderately wide row.

The leaves are medium green in color, or are approximately Forest Green (Plate XVII), or varying from Varley's Green (Plate XVIII) to Forest Green (Plate XVII), to Cerro Green (Plate V), depending mainly on soil fertility, but also depending on other soil conditions, exposure, and weather and climatic conditions. The leaves are medium in size, slightly glossy to glossy, slightly cupped, and medium in rugosity. The terminal leaflet overlaps the lateral leaflets, and the lateral leaflets slightly overlap at the base of the leaf. A few leaves have 4 leaflets instead of the normal 3. The flowers are perfect. The date of the first blossoms in 1973 at Champaign, Ill., was April 29.

At Champaign, Ill., my new variety of strawberry plant begins to mature its fruit early and at about the same time as Premier (Howard 17) and Sunrise. The date of the first picking in 1973 at Champaign, Ill., was May 25. The harvesting period is medium in length. The berries are well formed throughout the bearing season.

The fruit is medium red to medium dark red, or is approximately Carmine Red (Plate I), or varying from Nepal Red (Plate I) to Carmine Red (Plate I) to Oxblood Red (Plate I), depending mainly on exposure, but also depending on soil, weather, and climatic conditions. The fruit is large at the beginning of the season and small at the end of the picking season. The patented variety, Wray Red (Plant Pat. No. 101), is larger (large to extra large); moreover, a large average size is sustained on Wray Red until the end of the picking season. The fruit of my new variety is wedge or blunt wedge to conic or blunt conic in shape, and is not necked. The first berries are wedge or blunt wedge. Later they are conic to blunt conic. At the end of the season, the berries of Premier (Howard 17) are definitely long conic. The secondary and later berries of Sunrise are definitely slightly necked. The fruit of my new variety is slightly glossy, slightly soft, and attractive in appearance. The skin of the patented variety, Wray Red, is remarkably tough and its flesh is extra solid.

The calyx is large. Most sepals are 3-toothed instead of single-toothed. The achenes are about flush with the surface, and are yellow to red depending on exposure.

Under the conditions existing where my new variety of strawberry plant was reproduced and tested, the flesh of the berry is medium red. The fruit is subacid, and is slightly above average in flavor.

The strawberry above described, and the plant producing it, of course, may vary in slight details, depending on soil, weather, and climatic conditions.

What I claim is:

1. A new and distinct variety of strawberry plant substantially as herein shown and described, characterized by its high productivity, by its vigorous growth, and by its early season of maturity.

References Cited

UNITED STATES PATENTS

P.P. 101 8/1934 Wray ---------- Plants—48

ROBERT E. BAGWILL, Primary Examiner